United States Patent [19]

Coe et al.

[11] 4,297,577

[45] Oct. 27, 1981

[54] RADIATION DETECTION OF GAS COMPOSITIONS

[75] Inventors: Charles D. Coe, Barlow; Philip Wright, Dronfield Woodhouse, both of England

[73] Assignee: Land Pyrometers Limited, Sheffield, England

[21] Appl. No.: 99,008

[22] Filed: Nov. 29, 1979

[30] Foreign Application Priority Data

Nov. 29, 1978 [GB] United Kingdom ............ 846533/78

[51] Int. Cl.³ .............................................. G01J 1/00
[52] U.S. Cl. ..................................... 250/343; 250/345
[58] Field of Search ............... 250/343, 344, 345, 351; 356/435, 438, 439

[56] References Cited

U.S. PATENT DOCUMENTS

| | | | |
|---|---|---|---|
| 2,534,657 | 12/1950 | Bray | 250/343 |
| 3,678,262 | 7/1972 | Herrmann | 250/339 |
| 3,679,899 | 7/1972 | Dimeff | 250/343 |
| 3,793,525 | 2/1974 | Burch et al. | 250/343 |
| 3,805,074 | 4/1974 | McCormack | 250/343 |
| 3,869,613 | 3/1975 | Link et al. | 250/343 |
| 3,878,107 | 4/1975 | Pembrook et al. | 250/343 |
| 3,916,195 | 10/1975 | Burch et al. | 250/343 |
| 3,926,527 | 12/1975 | Pembrook et al. | 250/339 |
| 4,075,481 | 2/1978 | Stoft et al. | 250/343 |

FOREIGN PATENT DOCUMENTS 1486673  9/1977  United Kingdom .

OTHER PUBLICATIONS

Von Dr. W. Schaefer, *Ultrarol–Analysatoren und andere Betriebsphotometer*, VDI–Berichte Nr. 97, 1966.

*Primary Examiner*—Alfred E. Smith
*Assistant Examiner*—Janice A. Howell
*Attorney, Agent, or Firm*—Lowe, King, Price & Becker

[57] ABSTRACT

The invention relates to gas monitoring. Hitherto gas, such as flue gas has been analysed either by sampling and analysing the sample or by a spectrometer. However sampling is unreliable, and spectrography involves sensitive and expensive equipment needing extensive protection against vibration. In the invention, gas is monitored in situ by providing an infra red source and an infra red detector spaced across a gas flow, with a filter cell filled with the gas component to be monitored disposed between them. The detector detects radiation direct from the source and passing through the filter cell, and the outputs from the detector are fed to a differencing and dividing circuit to provide an output that is a function of the amount of monitored gas component in the gas flow.

1 Claim, 7 Drawing Figures

RADIATION DETECTION OF GAS COMPOSITIONS

This invention relates to the monitoring of gas and is particularly concerned with the selective determination of particular constituents of the gas.

There are many applications where gas must be analysed, e.g., in a flue gas there can be a carbon monoxide content, the quantity of which can give an accurate assessment as to whether or not a burner is operating at, above, or below optimum efficiency. There are also other applications where gases are known to contain an obnoxious or poisonous content and which must be closely controlled.

Equipment that is currently commercially available, e.g., for CO monitoring of boiler or furnace waste gas, generally falls into two categories, those in which the gas is first sampled and the sample analysed, and those which monitor the gas in-situ.

Most conventional equipment falls into the category where sampling is first effected, the gas being sampled through a filter probe to remove solid particles, then dried to remove any condensates, and finally passed to the analyser itself. The analyser would normally embody any one of many known techniques for analysis such as photometry, spectroscopy, filter reduction and chromatography. The major disadvantage of such techniques lies in the gas sampling itself, the analysers themselves usually being very adequate. Sampling systems generally require a considerable amount of maintenance and are known to be unreliable.

So far as in-situ monitoring is concerned, equipment is available but which in the main operates on a spectrometer principle for the simultaneous analysis of a number of gases usually CO, $SO_2$, $NO_x$, and $CO_2$. Although the actual analysis of the gas can be effected with reasonable accuracy, a problem inherent in spectrometers is that they tend to be very sensitive instruments which need extensive protection against vibration. For this reason such instruments when used in-situ tend to be of great bulk and the spectrometer itself must be mounted on a very substantial base. Optical alignment is critical requiring difficult and sensitive setting up and maintenance. Such equipment also tends to be expensive, automatically providing more information than is strictly required.

According to the present invention, equipment for the monitoring of gas in-situ comprises an infra red source adapted to be located in ducting or the like through which the gas to be analysed passes, a detector spaced from the infra red source, a band-pass filter between the detector and the source to restrict incoming radiation to a predetermined wavelength range, and a filter cell adapted to be positioned in the radiation path between the detector and the source, filled with the gas component requiring analysis, the detector being connected in a circuit capable of measuring radiation direct from the source and passing through the gas component filter cell, determining the difference between the two levels of radiation dividing the difference by either of the levels of radiation received by the detector, to provide an output from the said circuit that is a function of the amount of monitored gas present in the gas flow.

Preferably, and to ensure that the signals received by the detector is not distorted by absorption of radiation by the filter cell windows or indeed by dirt contamination of the windows, a second reference cell is provided filled with a gas component which does not absorb radiation over the wave-lengths selected by the band-pass filter.

The gas component filter cell and the reference cell when provided may each be permanently located in the radiation path, and when two radiation paths would be required one for each cell, with two detectors, again one for each cell. The two radiation paths can be provided by two separate sources or by employing a beam splitter in the radiation from a single source. Alternatively with a single source of radiation each gas component filter cell can be mounted for selective introduction into the radiation path alternately with the other.

Preferably the infra red source is an electrically heated plate, which can be protected by an infra red transmissive window, e.g., germanium and can be mounted in an opening to one side of the ducting. The detector is preferably a pyroelectric detector such as lithium tantalate, a form of detector offering high sensitivity and stability with low noise. With certain types of detector such as a lithium tantalate detector which is an a.c. detector and does not function with direct energy, a chopper blade must be provided between the detector and the source to chop incoming radiation to a predetermined frequency, and the chopper blade can also form part of the self-contained unit. The detector, chopper blade (when provided), and band-pass filter along with the electronic circuits may be formed as a self-contained unit for mounting at the opposite side of the boiler ducting to the infra red source, or the necessary electronic circuits may form a separate self-contained unit adapted to be located in any convenient position with the audible or visual signalling means similarly mounted where-ever convenient. Alternatively, the radiation source and the detector can be formed as a single unit of generally tube-like character with the radiation source at one end and the detector at the other, and with the tube pervious to gas. This allows the tube to be inserted into a flue gas when testing is required. It is still further possible within the spirit of the invention to provide both the infra red source and the or each detector to one side of a flue, and for infra red radiation to be transmitted across the flue gas to a reflector and back to the detector. Within this possibility, the reflector can be mounted on the flue gas wall to one side and the source and detector mounted on the flue gas wall to the opposite side. It would be equally possible to mount the source and the detector at one end of the tube and the reflector at the opposite end of the tube with the tube again being pervious to gas and capable of insertion into the flue gas.

When the two filter cells are mounted in line, it is preferred that they are secured to a solenoid, the reciprocal movement of which repeatedly introduces first one and then the other filter cell into the radiation path. By switching the gas component filter cell in and out of the radiation path alternatively with the inert gas filter cell, the difference in signals from the detector is a function of the concentration of the particular gas in the flue. By dividing the difference in signal by one or other of the signals themselves, the final output from the circuits is again a function of the concentration of the gas, and there is the substantial reduction, if not elimination, of problems of drift of calibration and temperature coefficient, and the avoidance of major problems caused by dirt coatings on necessary lenses utilised to focus the radiation on to the detector.

The invention therefore provides analysing equipment that is compact, rugged and relatively inexpensive.

As a further possibility within the invention, in a form of construction where two detectors are provided, each can be provided with a pair of in-line gas cells for selective introduction into the radiation path but with the movement of the cells synchronized in antiphase. This allows the possibility of the provision of substantially continuous readings of gas under analysis, and has the additional advantage that any stray fume passing up the stack and which could disturb the readings in a single detector system results in readings by the two detectors which are self-cancelling to a large extent so that accurate readings for the gas under analysis can be maintained despite the presence of fume.

It is obviously advantageous to periodically check the calibration of the monitoring device of the invention. It is therefore preferred to provide reference means comprising a second infra red source which has a fixed concentration of gas or no gas at all enclosed in a sight path which sight path can be directed into the monitoring device of the invention at predetermined intervals to allow the monitoring device to give readings for a predetermined gas concentration and which can then be utilised to determine the accuracy of the equipment and allow such calibration as is required.

The monitoring devices as discussed above all involve the use of a separate source of infra red radiation. It will however be understood that it will be possible in certain circumstances to allow the radiation emitted by hot gas itself to be used as the source directed at the detector.

One embodiment of the invention will now be described with reference to the accompanying drawings, in which.

Figure 1:
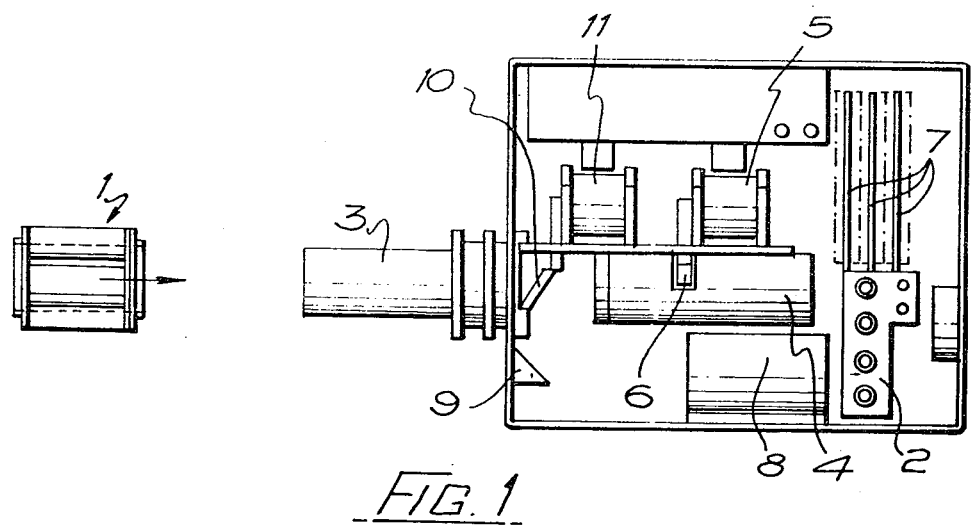
FIG. 1 is a front elevation of the monitoring device of the invention.

In FIG. 1 a monitoring device for the monitoring of gas in-situ has an infra red source 1 adapted to be located in ducting or the like (not shown) through which the gas to be analysed passes and a detector/signal processor unit 2 adapted to be located in spaced relationship from the infra red source. The unit 2 has a sight tube 3 adapted to focus incoming radiation from the infra red source on a lithium tantalate detector head 4. A rotary push/pull solenoid 5 supports and locates a filter cell 6 filled with the gas component to be analysed and a further dummy filter cell (not shown) alternately in the radiation path from the radiation source to the detector head. The unit further includes a chopper blade and band-pass filter between the detector of the detector head 4 and the infra red source. Printed circuit boards 7 containing the circuitry to provide control over the operation of the solenoid 5 and the processing of the signals received from the detector head are also provided in the units.

To provide for auto-calibration, the signal processor unit 2 can also include a further infra red source 8, which through mirrors 9 and 10 can direct infra red radiation at the detector head. The mirror 9 is fixed and the mirror 10 mounted on a rotary solenoid 11 to keep the mirror 10 in an inoperative position during normal use of the unit.

Figure 2:
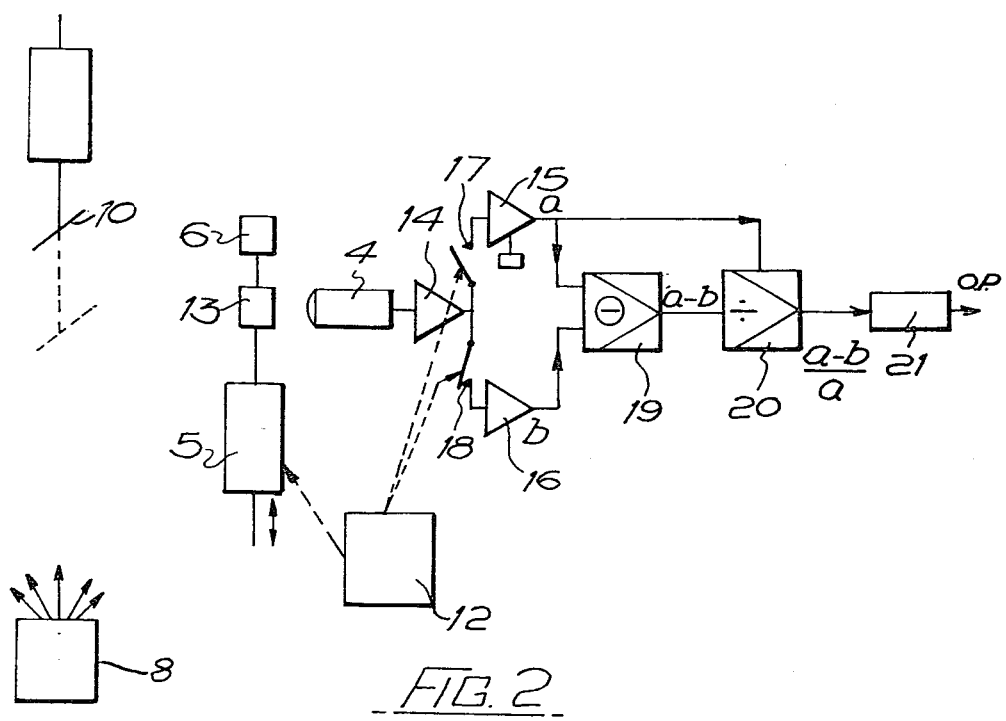
FIG. 2 is a block diagram of the circuitry of the monitoring device of FIG. 1.

FIG. 2 shows the circuitry of the unit 2 in block diagram form. Thus, the solenoid 5 is driven by a drive and timing circuit 12 to bring the filter cell 6 and the dummy cell 13 in the radiation path. The signals received by the detector head 4 are fed to a pre-amplifier 14, the output from which is fed either to a first sample and hold circuit 15 or a second output sample and hold circuit 16. The drive and timing circuit 12 also controls two switches 17, 18 such that when the dummy cell 13 is in the radiation path the signal is fed to the sample and hold circuit 16 and when the filter cell 6 is in the radiation path the signal is fed to the sample and hold circuit 15. The output from each sample and hold circuit is fed to a differencer circuit 19 where the two signal values are subtracted, one from the other, the output from the differencer being fed to a divider circuit 20 to which is also fed the output from the sample and hold circuit 15. The output from the divider circuit 20 is fed to a lineariser 21, the output from which can be utilised to provide an audible or visual signal showing the extent of the monitored gas in the gas flow under test and/or used as a control signal for adjustment of the operating conditions at the burner.

Figures 3, 4:
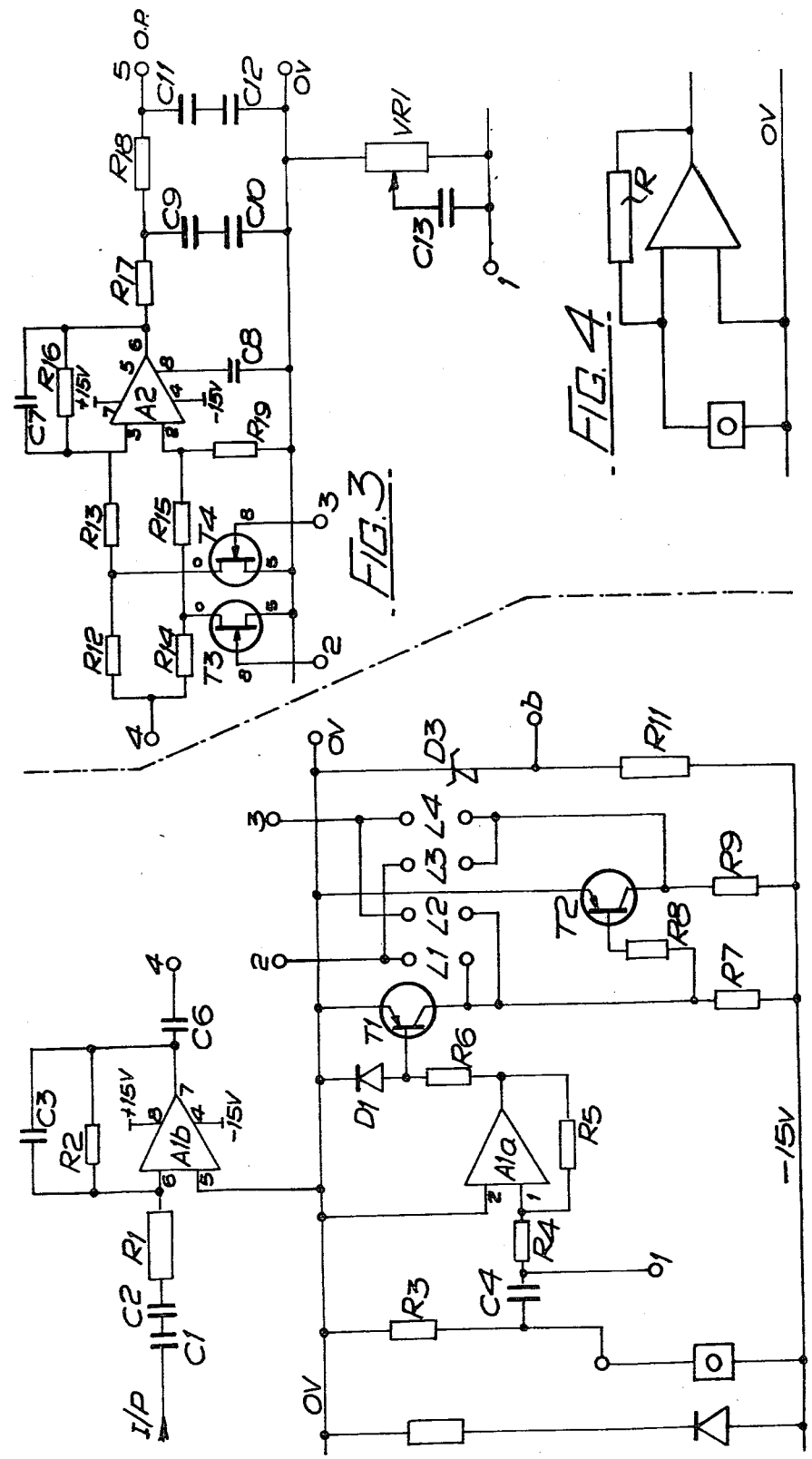
FIG. 3 is a circuit diagram of the detector head of FIG. 2.
FIG. 4 is a circuit diagram of the pre-amplifier of FIG. 2.
Figure 5:
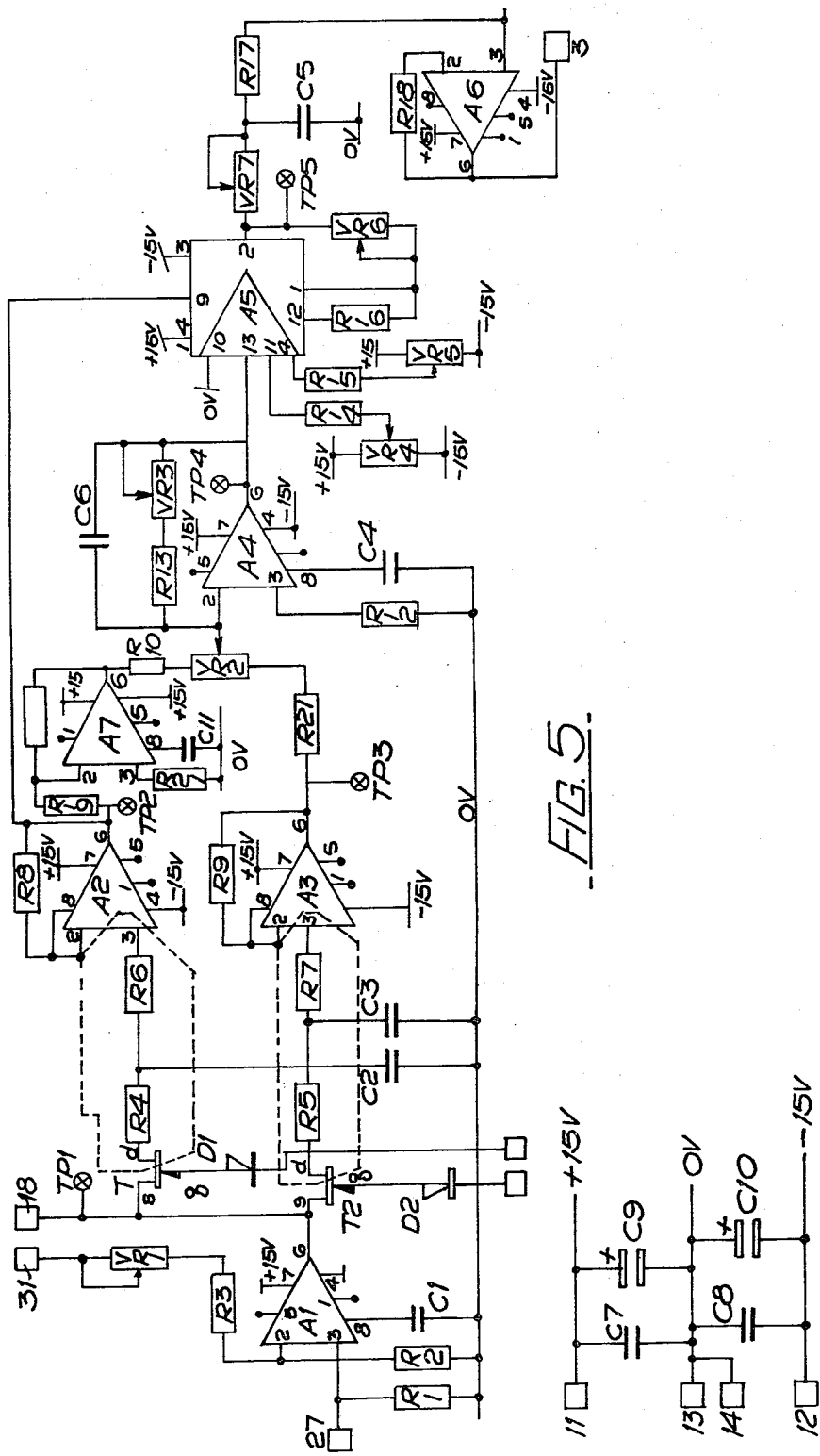
FIG. 5 is a circuit diagram of the signal processor.
Figure 6:
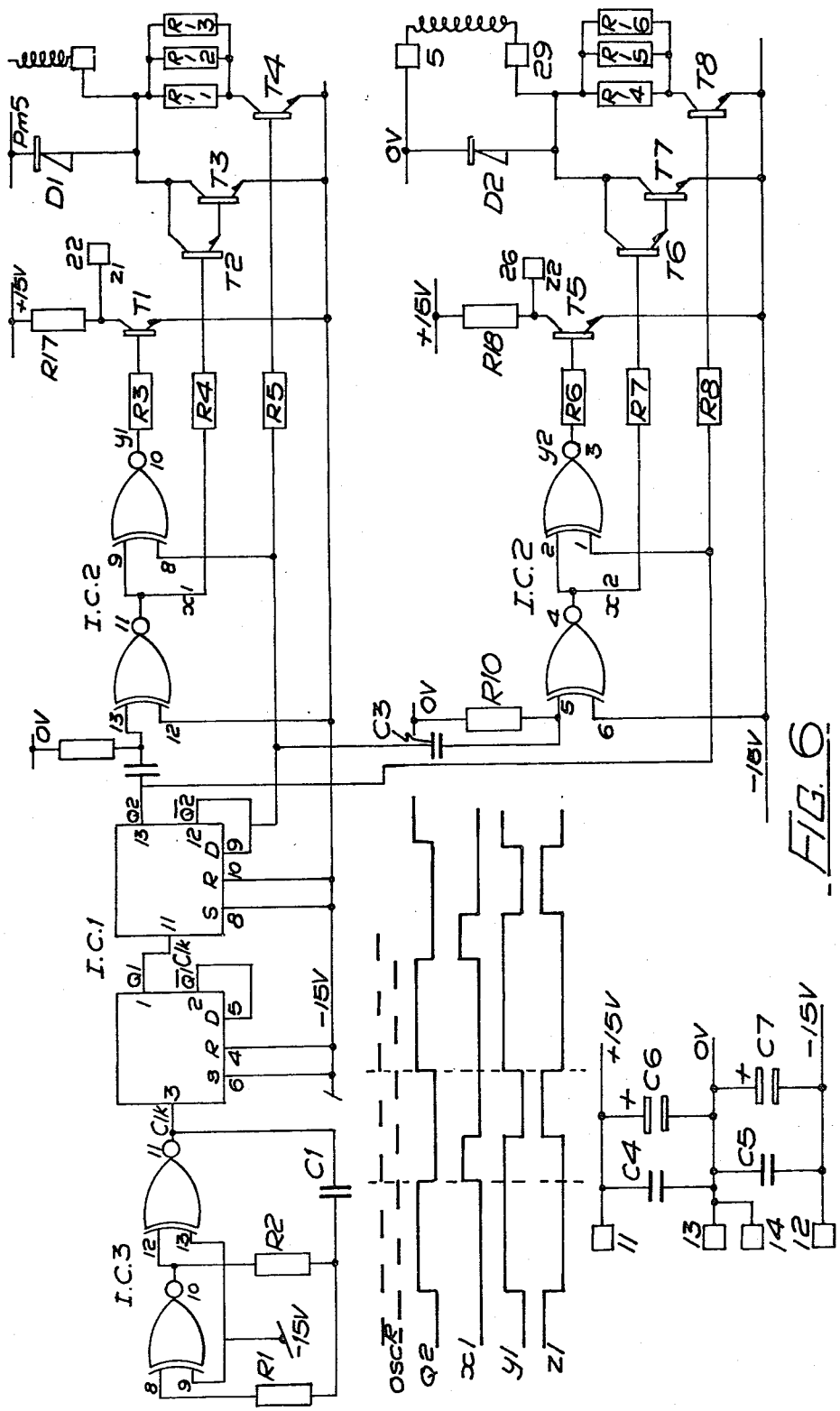
FIG. 6 is a circuit diagram of the device and timing circuit.

FIG. 3 shows the circuit of the detector head. For convenience it is shown in two parts and it will be understood that terminals 1-1, 2-2, 3-3 and 4-4 are connected. Thus, the signal from the detector head, a lithium tantalate detector, is fed to the input (I/P) the output from the circuit (O/P) being fed to the pre-amplifier 14, the circuit diagram for which is shown in FIG. 4. The switches 17, 18, sample and hold circuits 15 and 16, the differencing circuit 19 and the divider circuit 20 are all shown in FIG. 5, where A2 and A3 are the sample and hold sections, A7 and A4 are the differencer sections, and A5 the divider section. VR7, C5 and A6 constitute a damping circuit and whereby the output signal from the divider circuit can be damped.

Figure 7:
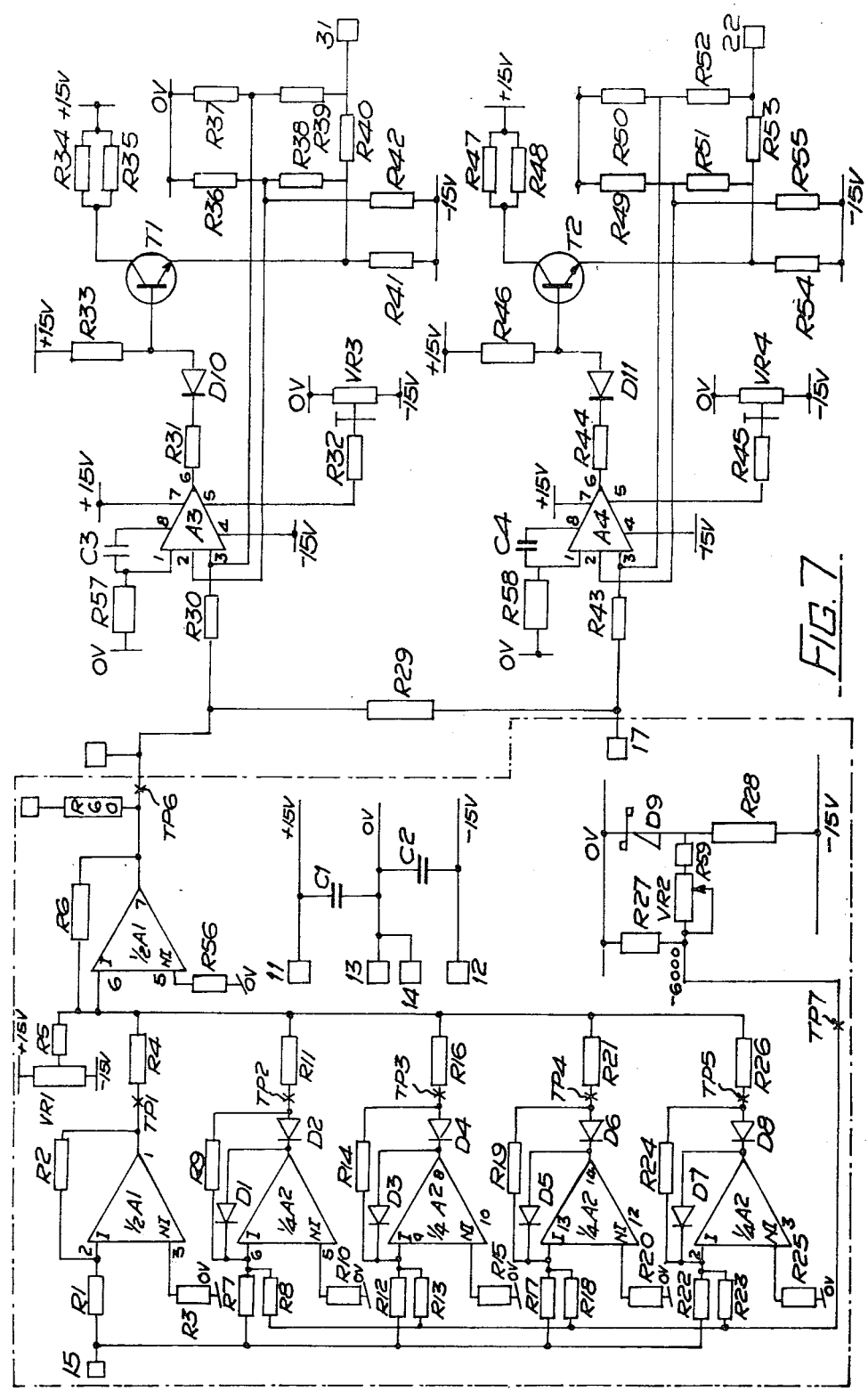
FIG. 7 is the circuit diagram of a lineariser.

The circuit diagram for the lineariser 21 is shown in FIG. 7, the lineariser having twin output stages, which can be current or voltage output as determined by appropriately setting the resistors.

We claim:

1. Equipment for the monitoring of gas in-situ comprising an infra-red source adapted to propagate a radiation beam through ducting or the like through which the gas to be analysed passes, a detector spaced from the infra red source responsive to radiation from the beam, a band-pass filter in the beam path to restrict beam radiation incident on the detector to a predetermined wavelength range, and a filter cell adapted to be positioned in the radiation path between the detector and the source, said cell being filled with the gas component requiring analysis, the detector and source being arranged such that the detector is responsive to beam radiation that passes in the ducting only through the gas to be analysed and to beam radiation that passes through the gas to be analysed and the cell, the detector being connected in a circuit including first means for measuring radiation passing through a first radiation path, second means for measuring radiation passing through a second radiation path, said gas to be analysed being in said first and second radiation paths, said gas component filter cell being in only said second radiation path, third means responsive to said first means and second means respectively for obtaining two levels of radiation, fourth means for determining a difference between the two levels of radiation, a fifth means for dividing the difference by either of the two levels of radiation received by the detector, an output of said circuit being a function of the amount of monitored gas present in the gas flow, including calibration means comprising a second infra red source generating radiation along a sight path, said sight path including an enclosure containing a fixed concentration of gas or no gas, said detector being selectively exposed in said sight path for equipment calibration.

* * * * *